(12) United States Patent
Chen et al.

(10) Patent No.: US 12,366,564 B2
(45) Date of Patent: Jul. 22, 2025

(54) WALL MOUNTABLE SENSOR MODULE WITH IMPROVED IAQ SENSOR RESPONSE TIME

(71) Applicant: Honeywell International Inc., Charlotte, NC (US)

(72) Inventors: Chao Chen, Beijing (CN); Yu Zhi Yan, Tianjin (CN); Hua Tang, Beijing (CN); Kaixuan Qin, Tianjin (CN); Zhi Yi Sun, Beijing (CN); Jian Wang, Tianjin (CN); Ke Wei Han, Tianjin (CN); Qixiang Hu, Tianjin (CN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 18/014,895

(22) PCT Filed: Oct. 11, 2022

(86) PCT No.: PCT/CN2022/124526
§ 371 (c)(1),
(2) Date: Jan. 6, 2023

(65) Prior Publication Data
US 2024/0241098 A1    Jul. 18, 2024

(51) Int. Cl.
*G01N 33/00*    (2006.01)
*F24F 11/30*    (2018.01)
(Continued)

(52) U.S. Cl.
CPC .......... *G01N 33/0031* (2013.01); *F24F 11/30* (2018.01); *G01N 33/004* (2013.01);
(Continued)

(58) Field of Classification Search
None
See application file for complete search history.

(56) References Cited

U.S. PATENT DOCUMENTS

| | | | | |
|---|---|---|---|---|
| 7,228,693 B2 * | 6/2007 | Helt | ......................... | F24F 11/77 |
| | | | | 236/44 C |
| 9,381,457 B2 * | 7/2016 | Nygren | .............. | B01D 46/0002 |
| 2023/0349875 A1 * | 11/2023 | Onghanseng | ...... | G01N 33/0031 |

FOREIGN PATENT DOCUMENTS

| | | | | |
|---|---|---|---|---|
| CN | 104360419 A | * | 2/2015 | ............. G01N 33/00 |
| CN | 208420624 U | | 1/2019 | |

(Continued)

OTHER PUBLICATIONS

Renesas Electronics Corporation, "Gas Sensor Module for TVOC and Indoor Air Quality", ZMOD4410 Datasheet, 25 pages, Jun. 30, 2021.

(Continued)

*Primary Examiner* — Peter J Macchiarolo
*Assistant Examiner* — Jermaine L Jenkins
(74) *Attorney, Agent, or Firm* — Seager, Tufte & Wickhem, LLP

(57) ABSTRACT

A wall mountable sensor module includes a housing defining an internal space that is segmented into a first internal space and a second internal space. The first internal space defines an air channel that extends from an air inlet to an air outlet. Two or more sensors are configured to be exposed to the air flow channel. A first sensor is configured to detect a first air parameter and a second sensor is configured to detect a second different air parameter, wherein the second sensor is situated downstream of the first sensor in the air flow channel. The sensor module includes a fan housed by the housing, the fan configured to cause an airflow to flow in through the air inlet, through the air flow channel thereby exposing each of the sensors to the airflow, and out through the air outlet.

20 Claims, 7 Drawing Sheets

(51) Int. Cl.
*F24F 11/88* (2018.01)
*F24F 110/64* (2018.01)
*F24F 110/66* (2018.01)
*F24F 110/70* (2018.01)

(52) U.S. Cl.
CPC ..... *G01N 33/0047* (2013.01); *G01N 33/0062* (2013.01); *F24F 11/88* (2018.01); *F24F 2110/64* (2018.01); *F24F 2110/66* (2018.01); *F24F 2110/70* (2018.01)

(56) References Cited

FOREIGN PATENT DOCUMENTS

| | | |
|---|---|---|
| CN | 214894698 U | 11/2021 |
| EP | 3800464 A1 | 7/2021 |

OTHER PUBLICATIONS

Sensirion, "Breaking the Size Barrier in CO2 Sensing", www.sensirion.com, Version 1, 21 pages, Mar. 2022.
Topband, "Laser Particle Sensor Module", www.gassensor.com.cn, Version V0.2, 20 pages, Apr. 20, 2020.

* cited by examiner

WALL MOUNTABLE SENSOR MODULE WITH IMPROVED IAQ SENSOR RESPONSE TIME

The present application claims priority to PCT International Application No. PCT/CN2022/124526, filed on Oct. 11, 2022, entitled "WALL MOUNTABLE SENSOR MODULE WITH IMPROVED IAQ SENSOR RESPONSE TIME", which is incorporated herein by reference.

TECHNICAL FIELD

The present disclosure relates generally to sensors, and more particularly to sensor modules that include a number of indoor air quality sensors within a housing.

BACKGROUND

A number of sensors are commonly used in building control systems. As an example, IAQ (Indoor Air Quality) sensors are used in a variety of building control systems including but not limited to building health systems and HVAC (Heating, Ventilating and Air Conditioning) systems. It would be desirable to have a sensor module that provides an improved sensor response time to facilitate better control by a building control system.

SUMMARY

The present disclosure relates generally to sensors, and more particularly to sensor modules that include a number of sensors within a housing. An example may be found in a wall mountable sensor module for monitoring two or more air parameters of a building for use in a building control system. The illustrative wall mountable sensor module includes a housing that has a front housing and a back housing that is configured to mate with the front housing to define an internal space of the housing. The front housing and the back housing segment the internal space into a first internal space and a second internal space, where the first internal space and the second internal space are separated from one another by one or more internal walls. The first internal space defines an air channel that extends from an air inlet in the housing to an air outlet of the housing. Two or more sensors are housed by the housing, and are configured to be exposed to the air flow channel. A first one of the two or more sensors is configured to detect a first one of the two or more air parameters and a second one of the two or more sensors is configured to detect a second different one of the two or more air parameters, wherein the second one of the two or more sensors is situated downstream of the first one of the two or more sensors in the air flow channel. The sensor module includes a fan housed by the housing. The fan is configured to cause an airflow to flow in through the air inlet in the housing, through the air flow channel thereby exposing each of the two or more sensors to the airflow, and out through the air outlet of the housing.

Another example may be found in a wall mountable sensor module for monitoring two or more air parameters of a building for use in a building control system. The illustrative wall mountable sensor module includes a housing configured to define an air flow channel extending through the housing from a first side of the housing to an opposing second side of the housing. The housing includes air apertures formed in the housing to provide fluid communication between the air flow channel and an environment outside of the housing. A Particulate Matter (PM) sensor is disposed within the housing that includes an air fan that is configured to blow air through the air flow channel. A $CO_2$ sensor is disposed within the housing and is positioned within the air flow channel. One or more additional sensors are disposed within the housing and are exposed to the air flow channel. One or more isolated sensors may be situated in the housing. The one or more isolated sensors are physically isolated from the air flow channel by internal structure of the housing, but exposed to the environment outside of the housing through one or more apertures in the housing.

Another example may be found in a wall mountable sensor module for monitoring two or more air parameters of a building for use in a building control system. The illustrative wall mountable sensor module includes a housing configured to define an air flow channel extending through the housing from a first side of the housing to an opposing second side of the housing. The housing includes air apertures formed in the housing to provide fluid communication between the air flow channel and an environment outside of the housing. A Particulate Matter (PM) sensor is disposed within the housing that includes an air fan that is configured to blow air through the air flow channel. A $CO_2$ sensor is disposed within the housing and is positioned within the air flow channel. A Total Volatile Organic Compounds (TVOC) sensor is disposed within the housing and is exposed to the air flow channel. One or more isolated sensors are situated in the housing. The one or more isolated sensors are physically isolated from the air flow channel by internal structure of the housing, but exposed to the environment outside of the housing through one or more apertures in the housing. A first printed circuit board is housed by the housing and bisects the air flow channel such that air passing through the air flow channel is bisected by the first printed circuit board and passes over both opposing major sides of at least part of the first printed circuit board. A second printed circuit board is electrically coupled with the first printed circuit board. The second printed circuit board extends into the air flow channel and hosts the PM sensor. A third printed circuit board is electrically coupled with the first printed circuit board. The third printed circuit board extends into the air flow channel and hosts the $CO_2$ sensor.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE FIGURES

The disclosure may be more completely understood in consideration of the following description of various examples in connection with the accompanying drawings, in which.

Figure 1:
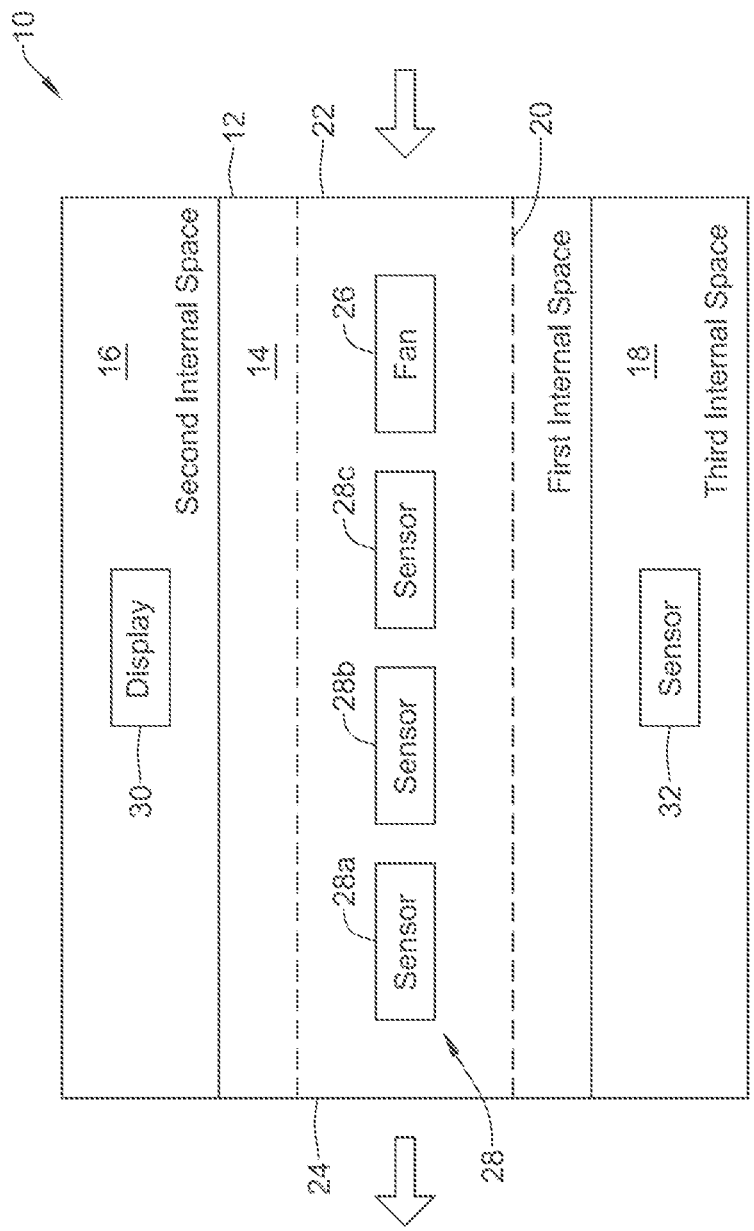
FIG. 1 is a schematic block diagram of an illustrative sensor module.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranged by endpoints includes all numbers subsumed within that range (e.g., 1 to 5 includes, 1, 1.5, 2, 2.75, 3, 3.8, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

FIG. 1 is a schematic block diagram showing an illustrative sensor module 10. The illustrative sensor module 10 includes a housing 12. As will be shown with respect to FIGS. 3 and 4, the housing 12 may include several different housing components that, together with one or more internal walls, divide the housing 12 into a first internal space 14 and a second internal space 16. In some cases, the housing 12 may also include a third internal space 18. In some instances, each of the first internal space 14, the second internal space 16 and the third internal space 18 may be used to house various sensor components at various positions relative to an air flow channel 20 that extends within the first internal space 14. Some sensors, for example, benefit from being exposed to air flow such as within the air flow channel 20 while other sensors may benefit from being isolated from the air flow channel 20.

In some cases, the air flow channel 20 extends from an air inlet 22 to an air outlet 24. The sensor module 10 may include a fan 26 that is disposed within the air channel 20, sometimes at a position close to the air inlet 22. As a result, the fan 26 is able to pull air through the air inlet 22 (which as will be discussed may include one or more apertures formed in a side wall of the housing 12), blow the air through the air channel 20 and out the air outlet 24. In some cases, the air inlet 22 may be on one side of the housing 12 while the air outlet 24 is positioned on a second, opposing, side of the housing 12. A number of sensors 28, individually labeled as 28a, 28b and 28c, may be disposed within the sensor module 10 such that at least some of the sensors 28 are deployed within the air channel 20, or are located such that at least some of the sensors 28 are exposed to air flowing through the air channel 20 as a result of the fan 26 operating. In some cases, one of the sensors 28 may be configured to detect a first air parameter and another of the sensors 28 may be configured to detect a second air parameter that is different from the first air parameter.

In some cases, one of the sensors 28 may be a particulate matter sensor such as a PM2.5 sensor. In some instances, the fan 26 may be a standalone fan, as shown. In some instances, the fan 26 may be incorporated into one of the sensors 28. As an example, the fan 26 may be incorporated into the sensor 28c, which may be a PM2.5 sensor. Another of the sensors 28 within the air channel 20 may be a $CO_2$ sensor. Another of the sensors 28 within the air channel 20 may be a TVOC (total volatile organic compound) sensor. These are just example sensor, and may be considered IAQ sensors. The sensors 28 may be arranged within the air channel 20 in any desired order or arrangement.

In some cases, the sensor module 10 may include components that do not benefit from being exposed to the air flow within the air channel 20. In some cases, the second internal space 16 may include such components. As an example, the sensor module 10 may include a display 30 that is disposed within the second internal space 16. The display 30 may simply be a display element that is configured to display information. In some cases, the display 30 may be a touchscreen display that not only displays information, but is able to accept user inputs as well.

In some cases, the sensor module 10 may include components that not only do not benefit from being exposed to the air flow within the air channel 20, but may in fact be negatively impacted by such air flow. In some cases, the third internal space 18 may include such components. As an example, the sensor module 10 may include a sensor 32 that is disposed within the third internal space 18 and as such is isolated from the air flow within the air channel 20. In some instances, the sensor 32 may be disposed proximate one or more apertures that are formed in a side wall of the housing 12, and in this way are passively exposed to an environment outside of the sensor module 10. In some cases, the sensor 32 may be a temperature sensor. The sensor 32 may also be a humidity sensor. In some cases, the sensor 32 may be another TVOC sensor. While a single sensor 32 is shown disposed within the third internal space 18, it will be appreciated that this is merely illustrative, as there may be one, two, three or more sensors 32 disposed within the third internal space 18.

Figure 2:
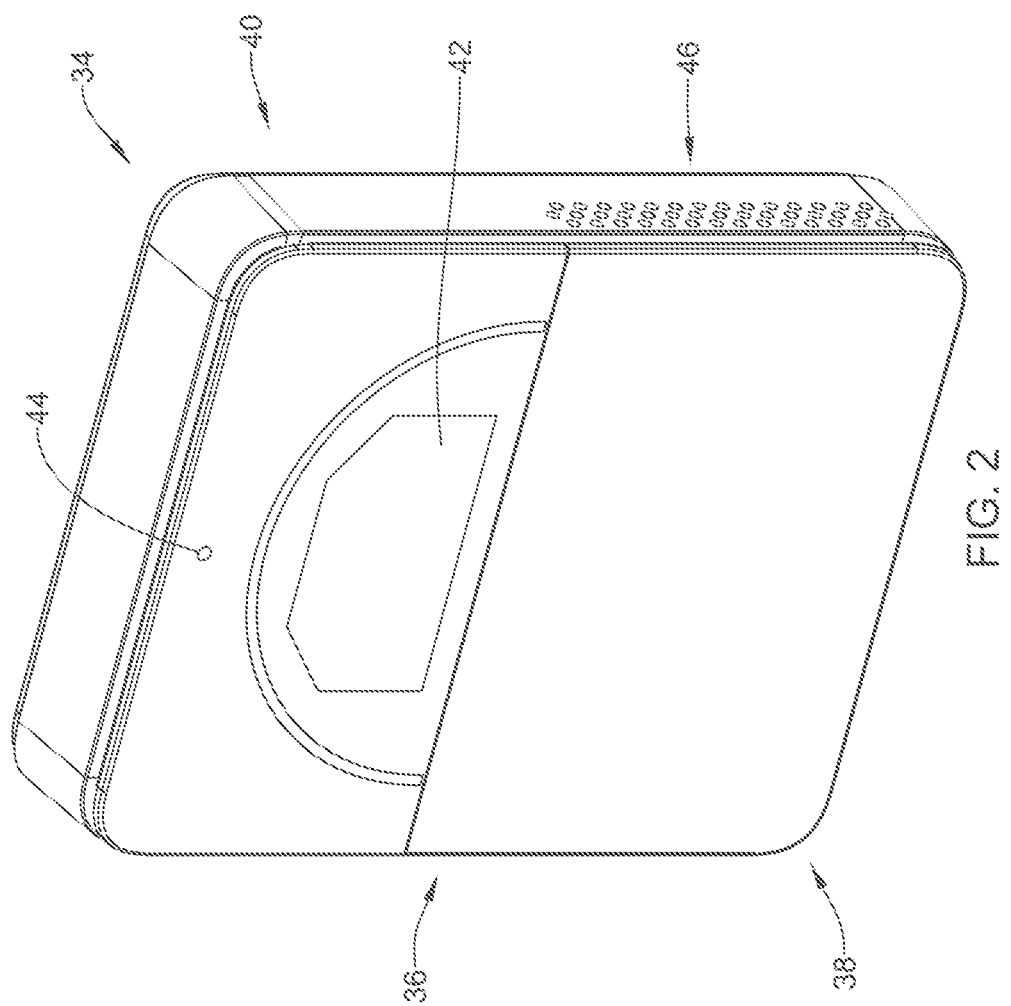
FIG. 2 is a perspective view of an illustrative sensor module.
Figure 3:
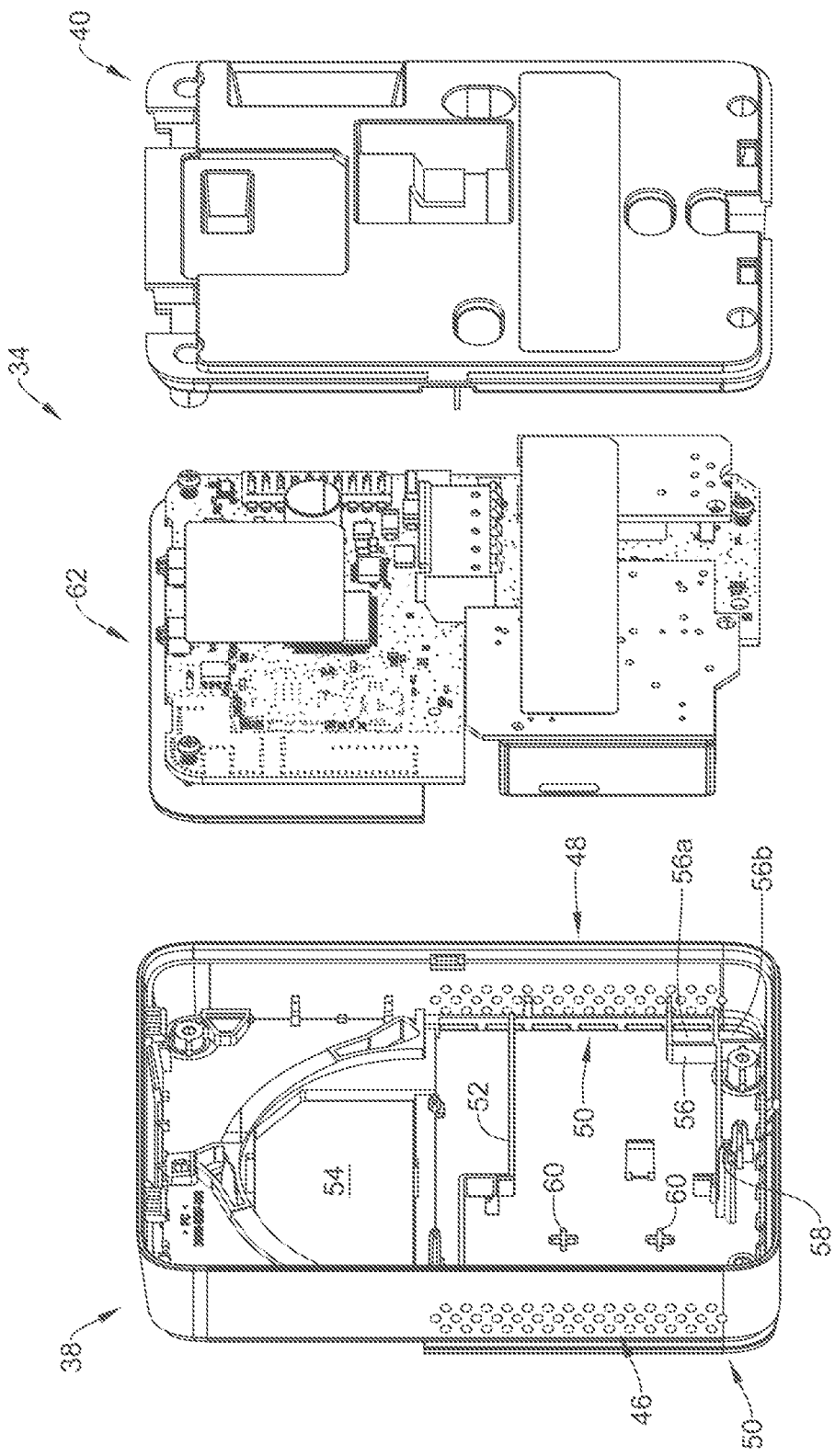
FIG. 3 is a partially exploded perspective rear view of the illustrative sensor module of FIG. 2.

FIG. 2 is a perspective view of an illustrative sensor module 34 while FIG. 3 is a partially exploded perspective rear view of the illustrative sensor module 34. The illustrative sensor module 34 may be considered as being an example of the sensor module 10. The sensor module 34 includes a housing 36 that may be considered as including a front housing 38 and a back housing 40. In some cases, the sensor module 34 may include one or more additional layers behind the back housing 40, such as a mounting plate, in order to facilitate mounting the sensor module 34 to a vertical surface such as a wall. The illustrative sensor module 34 includes a display 42 that may be considered as being an example of the display 30 (FIG. 1). In some cases, the sensor module 34 may also include a motion sensor 44.

The front housing 38 includes a number of air apertures 46 on a first side of the front housing 38 and a number of air apertures 48 on an opposing second side of the front housing 38. As an example, the air apertures 46 may be positioned proximate the air inlet 22 (FIG. 1) and the air apertures 48 may be positioned proximate the air outlet 24. In some cases, the front housing 38 may also include a number of apertures 50 that extend around a lower periphery of the front housing 38. In some cases, it may be one or more of the apertures 50 that provide passive airflow from a position outside of the sensor module 34 to the sensor(s) 32 that are disposed within the third internal space 18.

As seen in FIG. 3, an internal wall 52 extends in a rear-facing direction from the front housing 38. In some cases, the internal wall 52 may help to divide the first internal space 14 (FIG. 1) from the second internal space 16. The illustrative front housing 38 includes a display aperture 54 that is adapted to accommodate the display 42. An L-shaped internal wall 56 extends in a rear-facing direction from the front housing 38 and may be considered as defining a first isolated space 56a and a second isolated space 56b. The first isolated space 56a and the second isolated space 56b may be considered as being example of the third internal space 18 that, as discussed, is physically isolated from the air channel 20. Each of the first isolated space 56a and the second isolated space 56b may be considered as being proximate one of the aperture 50 such that each of the first isolated space 56a and the second isolated space 56b are passively in fluid communication with the environment outside of the sensor module 34. An internal wall 58 extends in a rear-facing direction from the front housing 38 and may be considered as helping to define part of the first internal space 14.

In some cases, the front housing 38 may include one or more isolation members 60 that may contact one of the internal component such as a fan 26 in order to provide vibration damping. When the sensor 28c (FIG. 1) incorporates the fan 26 into a PM2.5 sensor, the one or more isolation members 60 may contact the PM2.5 sensor in order to provide vibration damping. The isolation members 60 may help to dampen vibration caused by the fan 26 and to help isolate such vibration from other components of the sensor module 34.

The illustrative sensor module 34 includes an electronics assembly 62 that will be discussed in greater detail with respect to FIGS. 5, 6 and 7. The electronics assembly 62 includes the sensors 28 (FIG. 1) and 32, for example, as well as the fan 26. In some cases, as shown, the electronics assembly 62 includes several different printed circuit boards that serve to locate and electrically couple the sensors 28 and 32 and the fan 26 to other components of the sensor module 34. In some cases, the several different printed circuit boards may be used to help control air flow through the air channel 20, and in some cases, reduce the resistance to air flow through the air channel 20 to increase the air flow rate and thus reduce the response time of the sensor module 34.

Figure 4:
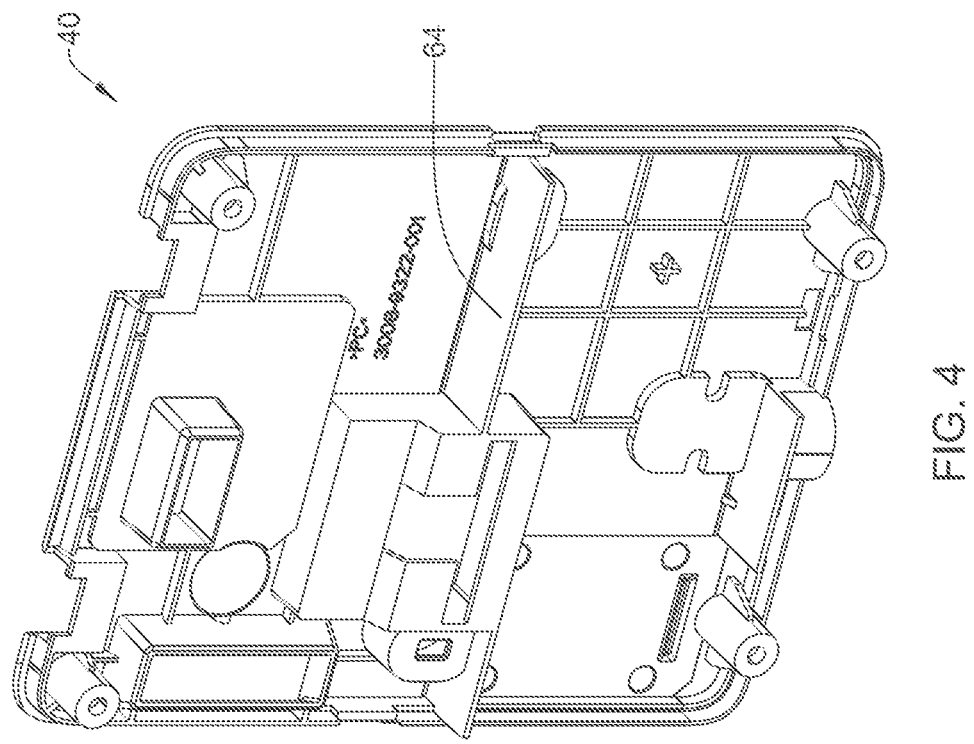
FIG. 4 is a front view of a rear housing forming part of the illustrative sensor module of FIG. 2.

FIG. 4 provides a front view of the back housing 40. The back housing 40 includes an internal wall 64 that extends from the back housing 40 in a front-facing direction. In some cases, the internal wall 64 cooperates with the back-facing internal wall 52 of the front housing 38, and one or more of the printed circuit boards forming the electronics assembly 62 to help divide the first internal space 14 (FIG. 1) from the second internal space 16 (and the third internal space 18).

Figure 5:
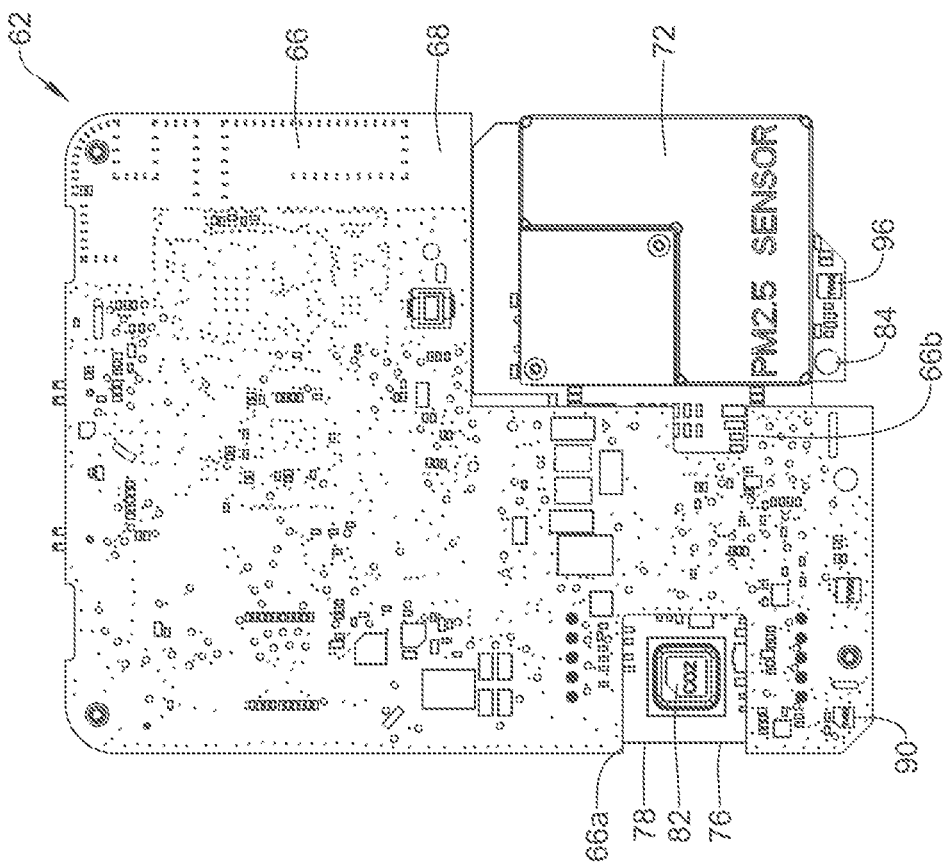
FIG. 5 is a front view of internal components of the illustrative sensor module of FIG. 2.
Figure 6:
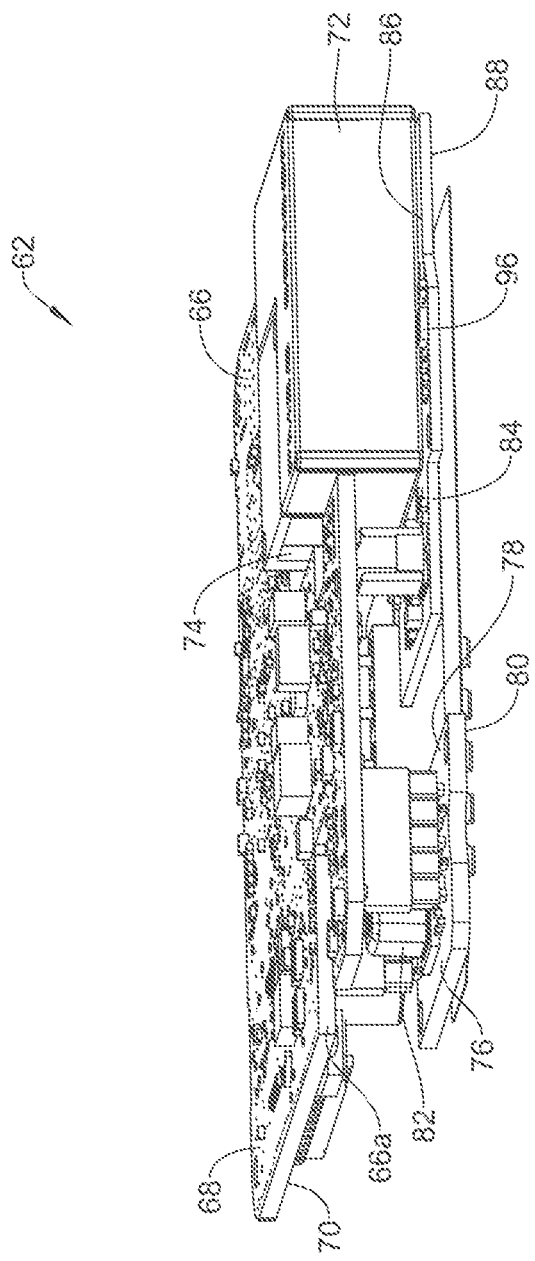
FIG. 6 is a perspective view of internal components of the illustrative sensor module of FIG. 2.
Figure 7:
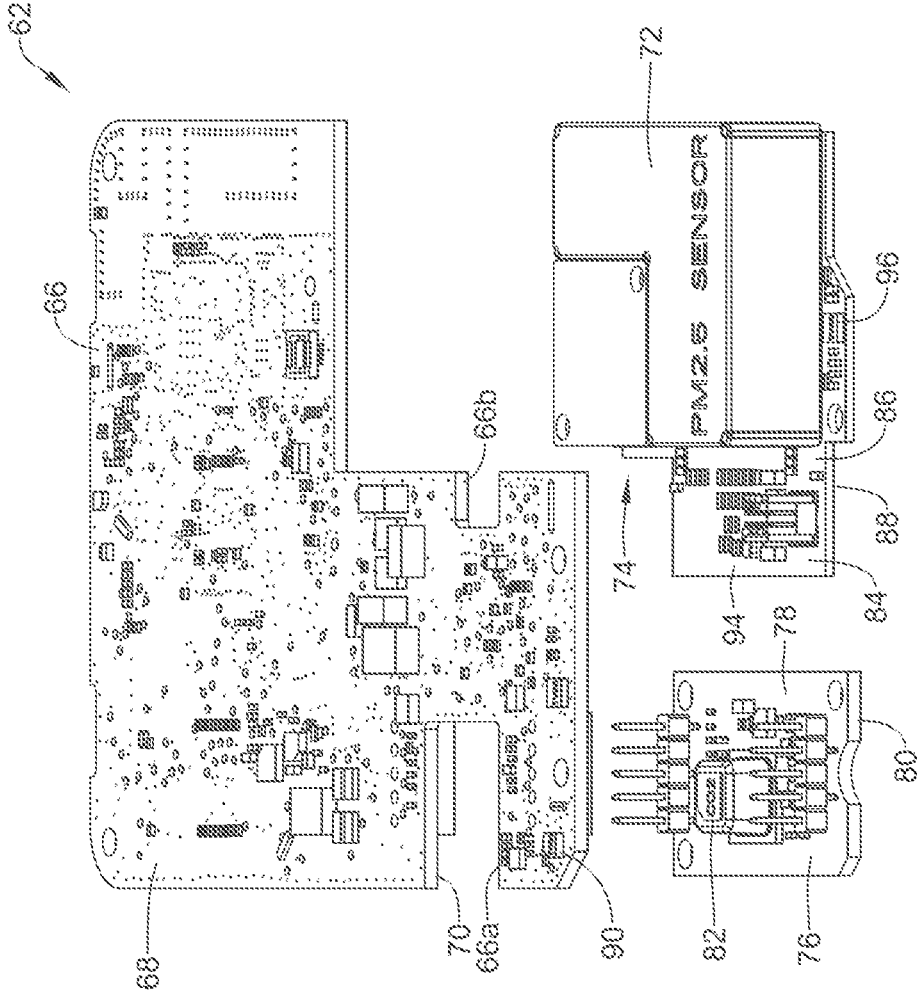
FIG. 7 is a partially exploded perspective view of internal components of the illustrative sensor module of FIG. 2.

FIGS. 5, 6 and 7 provide further details regarding the electronics assembly 62. FIG. 5 is a perspective front view of the electronics assembly 62, FIG. 6 is a side perspective view of the electronics assembly 62 and FIG. 7 is a partially exploded perspective front view of the electronics assembly 62. The illustrative electronics assembly 62 includes a first printed circuit board 66 that is housed by the housing 12. The first printed circuit board 66 includes a front side 68 that faces toward the front housing 38 and a back side 70 that faces toward the back housing 40. The first printed circuit board 66 may be considered as bisecting the air flow channel 20 such that air passing through the air flow channel is bisected by the first printed circuit board 66 such that the air passes over both the front side 68 and the back side 70 of the first printed circuit board 66. In this example, the first printed circuit board 66 extend into the first internal space 14, the second internal space 16 and in some cases the third internal space 18. In some cases, the display 42 may be electrically coupled to, and driven by, one or more components on the first printed circuit board 66.

In some cases, the electronics assembly 62 includes a PM 2.5 sensor 72 that includes a fan disposed within the PM2.5 sensor 72. The PM2.5 sensor 72 includes an outlet 74 on the left (in the illustrated orientation) of the PM2.5 sensor 72, as can be seen in FIG. 6. The air flow created by the fan within the PM2.5 sensor 72 exits the PM2.5 sensor and by virtue of the relative location of the outlet 74 relative to the first printed circuit board 66, the air flow exiting the PM2.5 sensor 72 and entering the air flow channel 20 is able to flow both over the front side 68 of the first printed circuit board 66 as well as flowing over the back side 70 of the first printed circuit board 66. In some cases, the first printed circuit board 66 may include a cutouts 66b that facilitates airflow between the front side 68 and the back side 70 of the first printed circuit board 66. The first printed circuit board 66 may include a cutout 66a that facilitates airflow between the front side 68 and the back side 70 of the first printed circuit board 66.

In some cases, the electronics assembly 62 includes a second printed circuit board 76 that is housed by the housing 12. The second printed circuit board 76 is electrically coupled with the first printed circuit board 66. The second printed circuit board 76 extends into the air flow channel 20 with a front side 78 of the second printed circuit board 76 facing towards the front housing 38 and a back side 80 of the second printed circuit board 76 facing towards the back housing 40. In some cases, at least part of the airflow flows between the first printed circuit board 66 and the second printed circuit board 76. In some cases, a $CO_2$ sensor 82 is mounted to the front side 78 of the second printed circuit board 76. In some cases, the cutout 66a formed in the first printed circuit board 66 may be at least partially aligned with the $CO_2$ sensor 82 in order to facilitate airflow around and over the $CO_2$ sensor 82.

In some cases, the electronics assembly 62 includes a third printed circuit board 84 that is housed by the housing 12. The third printed circuit board 84 is electrically coupled with the first printed circuit board 66. The third printed circuit board 84 extends into the air flow channel 20 with a front side 86 of the third printed circuit board 84 facing toward the front housing 38 and a back side 88 of the third printed circuit board 84 facing toward the back housing 40. In some cases, at least part of the airflow flows between the first printed circuit board 66 and the third printed circuit board 84. In some cases, the PM2.5 sensor 72 may be mounted onto the front side 86 of the third printed circuit board 84. In cases in which the fan 26 (FIG. 1) is distinct from the PM2.5 sensor 72, the fan 26 may additionally or alternatively be mounted onto the third printed circuit board 84.

In some cases, a temperature and/or relative humidity sensor 90 may be mounted on a lower left (in the illustrated orientation) corner of the first printed circuit board 66. It will be appreciated that this corresponds to the second isolated space 56b shown in FIG. 3. As a result, the temperature and/or relative humidity sensor 90 is isolated from the air flowing through the air channel 20, but is passively coupled with the environment outside of the sensor module 34 due to the apertures 50. A TVOC sensor 92 may be mounted on a lower edge of the first printed circuit board 66 at a location that will physically isolate the TVOC sensor 92 from the air flowing through the air channel 20, but allows the TVOC sensor 92 to be passively coupled with the environment outside of the sensor module 34 due to the apertures 50.

In some cases, another TVOC sensor 94 (visible in FIG. 7) may be mounted to the third printed circuit board 84. The TVOC sensor 94 is positioned such that it is exposed to the air flowing through the air channel 20. Another TVOC sensor 96 may be mounted to the third printed circuit board 84, at a position along a bottom edge of the third printed circuit board 84. The TVOC sensor 96 may be considered as being isolated from the air channel 20, but is passively coupled with the environment outside of the sensor module 34 due to the apertures 50.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A wall mountable sensor module for monitoring two or more air parameters of a building for use in a building control system, the wall mountable sensor module comprising:
   a housing including:
      a front housing;
      a back housing, wherein the back housing is configured to mate with the front housing to define an internal space of the housing;
      the front housing and the back housing segmenting the internal space into a first internal space and a second internal space, wherein the first internal space and the second internal space are separated from one another by one or more internal walls;
      the first internal space defining an air flow channel that extends from an air inlet in the housing to an air outlet of the housing;
   two or more sensors housed by the housing, the two or more sensors are configured to be exposed to the air flow channel, a first one of the two or more sensors is configured to detect a first one of the two or more air parameters and a second one of the two or more sensors is configured to detect a second different one of the two or more air parameters, wherein the second one of the two or more sensors is situated downstream of the first one of the two or more sensors in the air flow channel; and
   a fan housed by the housing, the fan configured to cause an airflow to flow in through the air inlet in the housing, through the air flow channel thereby exposing each of the two or more sensors to the airflow, and out through the air outlet of the housing.

2. The wall mountable sensor module of claim 1, wherein the air inlet in the housing and the air outlet of the housing are on opposing sides of the housing.

3. The wall mountable sensor module of claim 1, further comprising:
   a display housed by the housing, the display occupying at least part of the second internal space of the housing.

4. The wall mountable sensor module of claim 1, wherein the front housing and the back housing further segment the internal space into a third internal space, wherein the third internal space is internally isolated from the air flow channel of the first internal space by one or more internal walls of the housing, and wherein the third internal space is in fluid communication with an environment outside of the housing through one or more vents in the housing.

5. The wall mountable sensor module of claim 4, comprising a third one of the two or more sensors situated in the third internal space.

6. The wall mountable sensor module of claim 1, comprising:
   a first printed circuit board housed by the housing with a front side of the first printed facing toward the front housing and a back side of the first printed circuit board facing toward the back housing, wherein the first printed circuit board bisects the air flow channel such that air passing through the air flow channel is bisected by the first printed circuit board and passes over both the front side and the back side of at least part of the first printed circuit board.

7. The wall mountable sensor module of claim 6, wherein the first printed circuit board comprises one or more airflow cut-outs to facilitate airflow between the front side and the back side of the first printed circuit board.

8. The wall mountable sensor module of claim 6, comprising:
   a second printed circuit board housed by the housing, wherein the second printed circuit board extends into the air flow channel with a front side of the second printed circuit board facing toward the front housing and a back side of the second printed circuit board facing toward the back housing, wherein at least part of the airflow flows between the first printed circuit board and the second printed circuit board.

9. The wall mountable sensor module of claim 8, comprising:
   a third printed circuit board housed by the housing, wherein the third printed circuit board extends into the air flow channel with a front side of the third printed circuit board facing toward the front housing and a back side of the third printed circuit board facing toward the back housing, wherein at least part of the airflow flows between the first printed circuit board and the third printed circuit board.

10. The wall mountable sensor module of claim 9, wherein:
    the first one of the two or more sensors is mounted to the second printed circuit board, and the second one of the two or more sensors is mounted to the third printed circuit board.

11. The wall mountable sensor module of claim 10, wherein a third one of the two or more sensors is mounted to the first printed circuit board.

12. The wall mountable sensor module of claim 9, further comprising a display mounted to the first printed circuit board outside of the air flow channel.

13. The wall mountable sensor module of claim 10, wherein the fan is mounted to the third printed circuit board in the air flow channel.

14. The wall mountable sensor module of claim 1, wherein the two or more sensors comprise two or more of a particulate matter sensor, a Total Volatile Organic Compounds (TVOC) sensor, and a $CO_2$ sensor.

15. A wall mountable sensor module for monitoring two or more air parameters of a building for use in a building control system, the wall mountable sensor module comprising:
- a housing configured to define an air flow channel extending through the housing from a first side of the housing to an opposing second side of the housing, the housing including air apertures formed in the housing to provide fluid communication between the air flow channel and an environment outside of the housing;
- a Particulate Matter (PM) sensor disposed within the housing, the PM sensor including an air fan that is configured to blow air through the air flow channel;
- a $CO_2$ sensor disposed within the housing, the $CO_2$ sensor positioned within the air flow channel;
- one or more additional sensors disposed within the housing and exposed to the air flow channel; and
- one or more isolated sensors that are internally physically isolated from the air flow channel but exposed to the environment outside of the housing.

16. The wall mountable sensor module of claim 15, further comprising a first printed circuit board.

17. The wall mountable sensor module of claim 16, wherein the air flow channel is bisected by the first printed circuit board.

18. The wall mountable sensor module of claim 17, comprising:
- a second printed circuit board that is electrically coupled with the first printed circuit board, the second printed circuit board hosting the PM sensor; and
- a third printed circuit board that is electrically coupled with the first printed circuit board, the third printed circuit board hosting the $CO_2$ sensor.

19. The wall mountable sensor module of claim 18, further comprising one or more TVOC sensors mounted to the second printed circuit board.

20. A wall mountable sensor module for monitoring two or more air parameters of a building for use in a building control system, the wall mountable sensor module comprising:
- a housing configured to define an air flow channel extending through the housing from a first side of the housing to an opposing second side of the housing, the housing including air apertures formed in the housing to provide fluid communication between the air flow channel and an environment outside of the housing;
- a Particulate Matter (PM) sensor disposed within the housing, the PM sensor including an air fan that is configured to blow air through the air flow channel;
- a $CO_2$ sensor disposed within the housing, the $CO_2$ sensor positioned within the air flow channel;
- a Total Volatile Organic Compounds (TVOC) sensor disposed within the housing and exposed to the air flow channel;
- one or more isolated sensors that are internally physically isolated from the air flow channel but exposed to the environment outside of the housing;
- a first printed circuit board housed by the housing, the first printed circuit board bisecting the air flow channel such that air passing through the air flow channel is bisected by the first printed circuit board and passes over both sides of at least part of the first printed circuit board;
- a second printed circuit board that is electrically coupled with the first printed circuit board, the second printed circuit board extending into the air flow channel and hosting the PM sensor, and
- a third printed circuit board that is electrically coupled with the first printed circuit board, the third printed circuit board extending into the air flow channel and hosting the $CO_2$ sensor.

* * * * *